(12) United States Patent
Suzuki et al.

(10) Patent No.: US 9,134,253 B2
(45) Date of Patent: Sep. 15, 2015

(54) INSPECTING APPARATUS AND INSPECTING METHOD

(71) Applicant: Kabushiki Kaisha Toshiba, Minato-ku (JP)

(72) Inventors: Masaru Suzuki, Kuwana (JP); Hiroyuki Mizuno, Kuwana (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 43 days.

(21) Appl. No.: 14/167,227

(22) Filed: Jan. 29, 2014

(65) Prior Publication Data

US 2015/0062570 A1    Mar. 5, 2015

Related U.S. Application Data

(60) Provisional application No. 61/870,330, filed on Aug. 27, 2013.

(51) Int. Cl.
| | |
|---|---|
| *G01N 21/00* | (2006.01) |
| *G01N 21/94* | (2006.01) |
| *G03F 7/00* | (2006.01) |
| *G01N 15/02* | (2006.01) |
| *G01N 15/00* | (2006.01) |

(52) U.S. Cl.
CPC ............ *G01N 21/94* (2013.01); *G01N 15/0227* (2013.01); *G03F 7/00* (2013.01); *G01N 2015/0096* (2013.01)

(58) Field of Classification Search
CPC .............. G01N 21/00; G01N 15/0227; G01N 2015/0096; G03F 7/00
USPC ......................................................... 356/237.4
See application file for complete search history.

(56) References Cited

U.S. PATENT DOCUMENTS

| | | | |
|---|---|---|---|
| 7,218,383 | B2 | 5/2007 | Matsui |
| 2003/0184744 | A1* | 10/2003 | Isozaki et al. .............. 356/237.2 |

FOREIGN PATENT DOCUMENTS

| | | |
|---|---|---|
| JP | 2005-150527 | 6/2005 |
| JP | 2009-170721 | 7/2009 |
| JP | 2010-45317 | 2/2010 |
| JP | 2010-147264 | 7/2010 |

* cited by examiner

*Primary Examiner* — Roy M Punnoose
(74) *Attorney, Agent, or Firm* — Oblon, McClelland, Maier & Neustadt, L.L.P.

(57) ABSTRACT

According to one embodiment, an inspecting apparatus is provided with a contact position obtaining unit and an inspection status determining unit. The contact position obtaining unit obtains, by using an inspection result of whether there is a particle on an inspection surface of a holding object and coordinate information of a convex portion in an electrostatic chuck holding mechanism, a contact position of the inspection surface with the convex portion. The inspection status determining unit determines whether a size of the particle adhering to a contact region with the convex portion of the inspection surface is within an allowable range by using a first determining criterion value and determines whether the size of the particle adhering to a non-contact region with the convex portion of the inspection surface is within an allowable range by using a second determining criterion value larger than the first determining criterion value.

20 Claims, 13 Drawing Sheets

INSPECTING APPARATUS AND INSPECTING METHOD

CROSS-REFERENCE TO RELATED APPLICATIONS

This application is based upon and claims the benefit of priority from U.S. Provisional Application No. 61/870,330, filed on Aug. 27, 2013; the entire contents of which are incorporated herein by reference.

FIELD

Embodiments described herein relate generally to an inspecting apparatus and an inspecting method.

BACKGROUND

A wavelength of a light source used in an exposure apparatus becomes shorter as a semiconductor device is shrunk and an exposure apparatus (EUV exposure apparatus) which uses extreme ultraviolet light (hereinafter, also referred to as EUV light) with a wavelength of approximately 100 nm or shorter is increasingly applied to the semiconductor device. The EUV light has a property of being attenuated in an atmosphere and less easily transmitted through a material such as glass used as a mask of a conventional exposure apparatus. Therefore, EUV exposure is performed in general by using a reflective mask provided with a multilayer film such as Mo and Si in a vacuum chamber.

Since the EUV exposure is performed in the vacuum chamber in this manner, it is difficult to apply a method of holding an outer peripheral portion of the mask by a vacuum absorption chuck used in the conventional exposure apparatus as a mechanism to hold the mask. Therefore, a method of holding a rear surface side of the mask by an electrostatic chuck is used in general.

An electrostatic chuck holding mechanism has a structure in which an electrode layer is formed on a base body surface and a plurality of convex portions in contact with the mask rear surface is arranged on the electrode layer in a two-dimensional manner. The convex portions are arranged so as to be also in contact with the rear surface included in a pattern area of the mask. Therefore, a contact area between the electrostatic chuck holding mechanism and the mask rear surface becomes larger than that in a case of holding by the conventional vacuum absorption chuck. According to this, possibility that a particle adheres to the mask rear surface or the electrostatic chuck becomes higher. When the mask is held by using the electrostatic chuck holding mechanism in a state in which the particle adheres to the mask rear surface, flat mask clamping cannot be realized and there is a case in which an exposure pattern is not normally formed.

Therefore, an exposure process is performed after performing mask rear surface inspection and allowing the particle of a predetermined size or a predetermined number of particles to adhere to the mask rear surface.

DETAILED DESCRIPTION

In general, according to one embodiment, an inspecting apparatus which inspects whether there is a particle adhering to a surface on a side in contact with a convex portion of an electrostatic chuck holding mechanism of a holding object held by the convex portion is provided. The inspecting apparatus is provided with a contact position obtaining unit and an inspection status determining unit. The contact position obtaining unit obtains a contact position of an inspection surface with the convex portion by using an inspection result of whether there is the particle on the inspection surface of the holding object and coordinate information of the convex portion in the electrostatic chuck holding mechanism. The inspection status determining unit determines whether a size of the particle adhering to a contact region in contact with the convex portion of the inspection surface is within an allowable range by using a first determining criterion value and determines whether the size of the particle adhering to a non-contact region other than the region in contact with the convex portion of the inspection surface is within the allowable range by using a second determining criterion value larger than the first determining criterion value.

The inspecting apparatus and an inspecting method according to the embodiments are hereinafter described in detail with reference to the accompanying drawings. Meanwhile, the present invention is not limited to the following embodiments.

First Embodiment

Figure 1A:
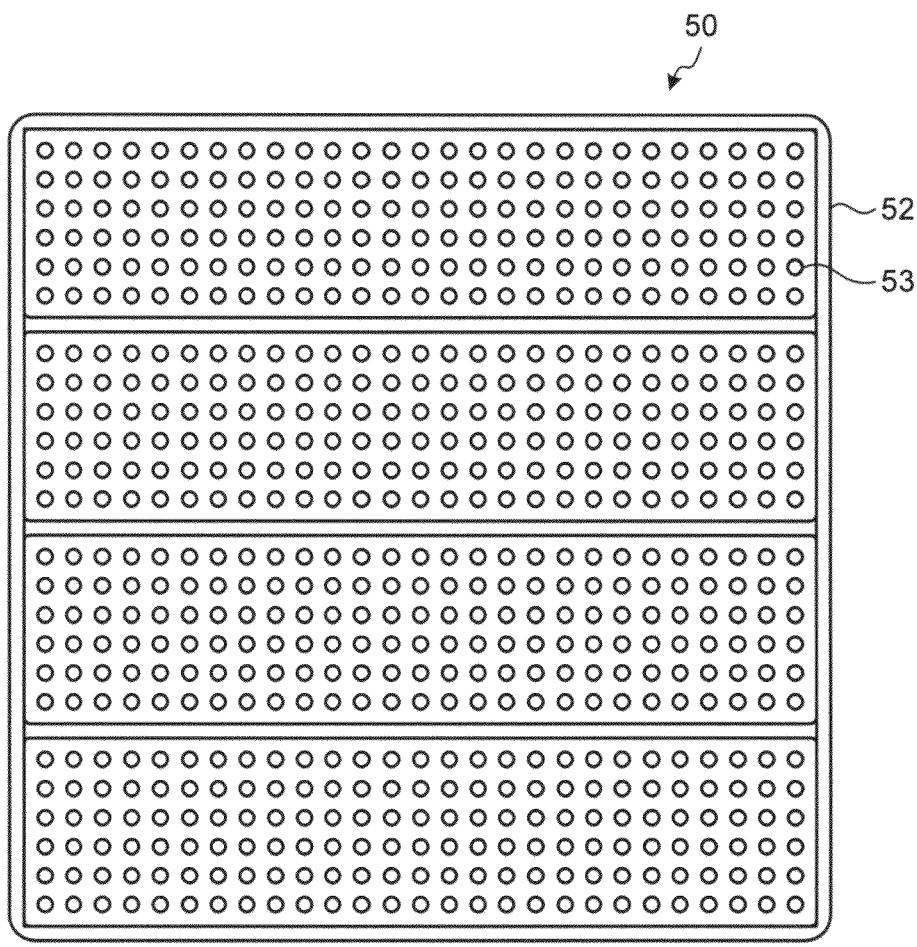
FIG. 1A is a top view of an example of an electrostatic chuck holding mechanism.
Figure 1B:
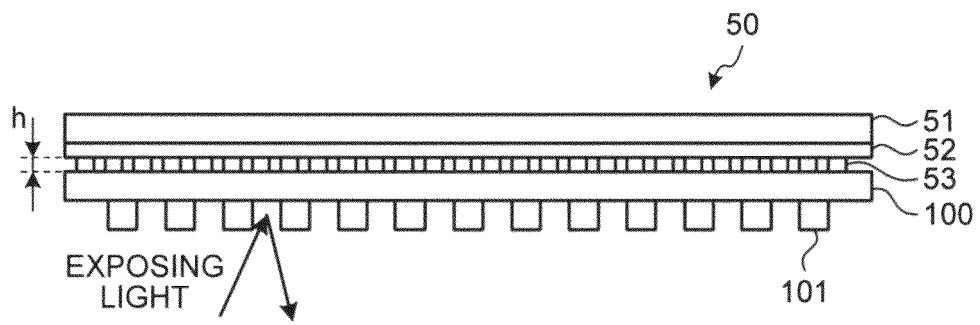
FIG. 1B is a side view of an example of a state in which a mask is held by the electrostatic chuck holding mechanism.

FIG. 1A is a top view of an example of an electrostatic chuck holding mechanism and FIG. 1B is a side view of an example of a state in which the electrostatic chuck holding mechanism holds a mask. An electrostatic chuck holding mechanism 50 has a structure in which a conductive layer 52 is provided on one main surface of a base body 51 with a flat plate shape. A plurality of convex portions 53 is provided on a surface of the conductive layer 52. A material such as glass and ceramics having very low thermal expansion may be used as the base body 51. A conductive material such as TiN and CrN may be used as the conductive layer 52 having the convex portion 53.

The convex portions 53 are arranged in a two-dimensional manner at a predetermined interval on one main surface of the base body 51. A height h of the convex portion 53 is 5 to 50 µm, for example, and a diameter of the convex portion 53 is approximately 1 mm. The convex portions 53 are arranged such that a contact area between the convex portions 53 and a mask 100 is approximately 1 to 5% of an area of the mask 100. Meanwhile, the diameter (area) of the convex portion 53 is exaggeratingly illustrated in FIG. 1A.

As illustrated in FIG. 1B, the electrostatic chuck holding mechanism 50 can fix the mask 100 by bringing the convex portion 53 of the electrostatic chuck holding mechanism 50 into contact with a rear surface of the mask 100 being a holding object and applying a voltage to the conductive layer 52. Meanwhile, the rear surface of the mask 100 is a surface on which a mask pattern 101 is not formed and is coated with a conductive substance such as CrN.

As illustrated in FIGS. 1A and 1B, the convex portions 53 are provided on an entire surface of the base body 51. That is to say, the convex portion 53 is in contact with the rear surface included in a pattern area of the mask.

In an EUV exposure apparatus the mask 100 is held by the electrostatic chuck holding mechanism 50 in a vacuum chamber and an exposure process is performed. In the electrostatic chuck holding mechanism 50, a large number of convex portions 53 are in contact with the rear surface of the mask 100 as described above and the contact area increases, so that it is highly possible that the particle adheres to the electrostatic chuck holding mechanism 50 or the rear surface of the mask 100. When the mask 100 to which the particle adheres is held by the electrostatic chuck holding mechanism 50, flat mask clamping cannot be realized and there is a case in which an exposure pattern is not normally formed. Therefore, conventionally, rear surface inspection of the mask 100 is performed and, when there is the particle not smaller than a predetermined size or when the number of the particles is not less than a predetermined number, the mask 100 is cleaned.

However, in this method, it is uniformly determined regardless of whether the position of the particle is in a contact position of the rear surface of the mask 100 with the convex portion 53 of the electrostatic chuck holding mechanism 50 or not. Therefore, there is a case in which the mask 100 is cleaned even when the particle is present in a region between the convex portions 53 and the flat mask clamping may be realized essentially.

Therefore, in the first embodiment, the contact position or an estimated contact position of the rear surface of the mask 100 with the convex portion 53 of the electrostatic chuck holding mechanism 50 is obtained in the rear surface inspection of the mask 100 and they are made a convex portion contact region. A region other than this is made a convex portion non-contact region. Then, they are superimposed on a particle map indicating a position in which the particle is present obtained as a result of the rear surface inspection of the mask 100 and it is determined whether to clean the mask 100 while changing a determining criterion value being an allowable size of the particle between the convex portion contact region and the convex portion non-contact region.

Figure 2:
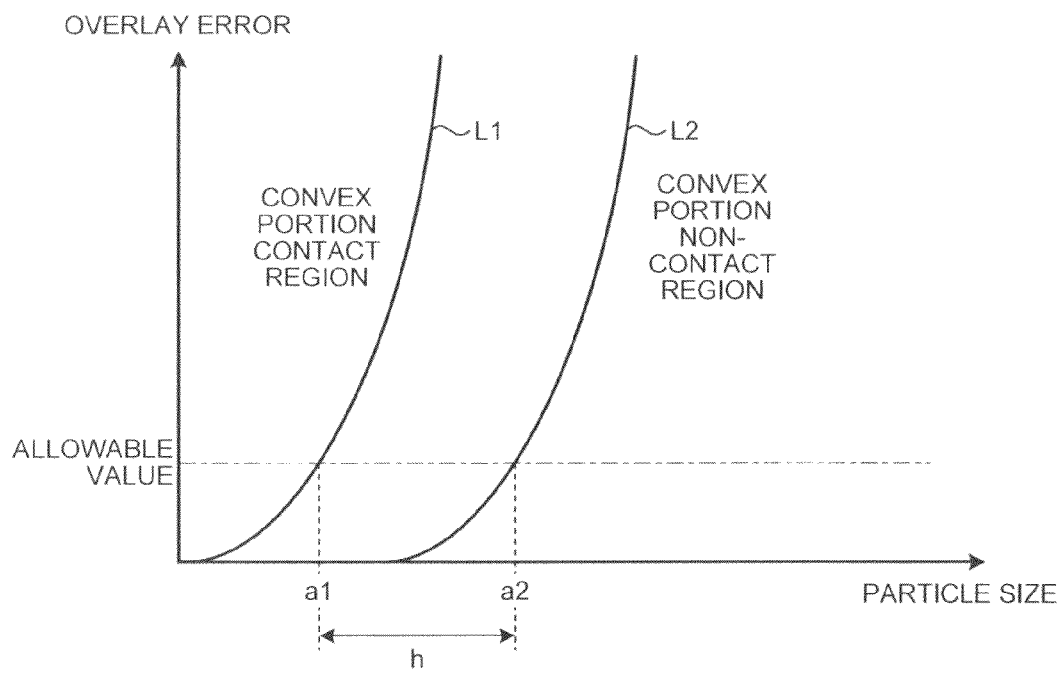
FIG. 2 is a view of an example of a concept of a determining criterion value according to a first embodiment.

FIG. 2 is a view illustrating an example of a concept of the determining criterion value according to the first embodiment. In the drawing, the size of the particle adhering to the rear surface of the mask 100 is plotted along the abscissa and an overlay error from an ideal position of a formed position of the pattern formed by the exposure process is plotted along the ordinate. In the convex portion contact region, the overlay error increases as the size of the particle on the convex portion contact region becomes larger. However, when the overlay error is not larger than a certain allowable value without an effect on subsequent formation of a semiconductor device, the size of the particle adhering to the rear surface of the mask 100 may be compared with the particle size corresponding to the allowable value.

As illustrated in FIG. 1B, there is a concave portion between the convex portions 53 of the electrostatic chuck holding mechanism 50. Therefore, when the particle enters a region between the convex portions 53, the particle size corresponding to the allowable value may be made larger than that in a case in which the particle adheres to the convex portion 53 by the height h of the convex portion 53. In FIG. 2, a curved line L2 indicating the overlay error with respect to the particle size in the convex portion non-contact region is obtained by parallel translation of a curved line L1 indicating the overlay error with respect to the particle size in the convex portion contact region rightward by the height h of the convex portion 53. While the particle size corresponding to the allowable value in a case in which the particle adheres to the convex portion contact region is a1, the particle size corresponding to the allowable value in a case in which the particle adheres on the convex portion non-contact region is a1+h=a2.

That is to say, in the first embodiment, it is determined whether to clean the mask 100 by comparing the particle size with the first determining criterion value a1 being the size of the particle with which the exposure pattern is within an allowable range even when there is the particle in the convex portion contact region. It is determined whether to clean the mask 100 by comparing the particle size with the second determining criterion value a2 being the size of the particle with which the exposure pattern is within the allowable range even when there is the particle in the convex portion non-contact region.

As a method of superimposing the convex portion contact region and the convex portion non-contact region on the particle map, a method of applying convex portion positional data indicating a formed position of the convex portion 53 of the electrostatic chuck holding mechanism 50 to the particle map, a method of obtaining the convex portion contact region and the convex portion non-contact region by calculation by using an already adhering particle or a trace of contact with the convex portion 53 obtained from the particle map and superimposing a result thereof on the particle map or the like may be used.

Figure 3:
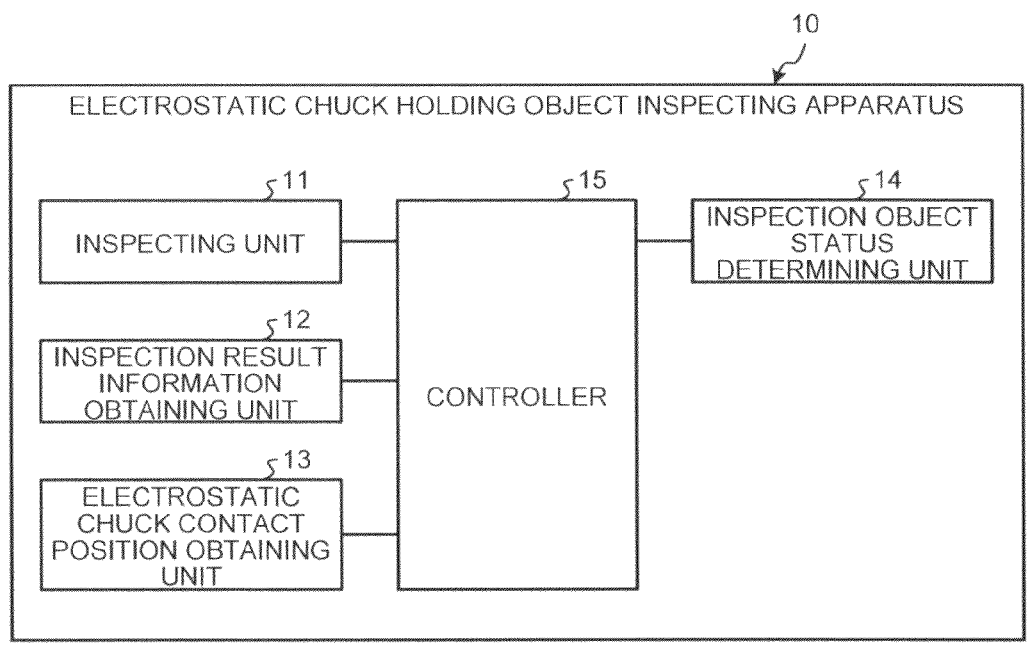
FIG. 3 is a schematic block diagram of a functional configuration of an electrostatic chuck holding object inspecting apparatus according to the first embodiment.

FIG. 3 is a schematic block diagram of a functional configuration of an electrostatic chuck holding object inspecting apparatus according to the first embodiment. An electrostatic chuck holding object inspecting apparatus 10 is provided with an inspecting unit 11, an inspection result information obtaining unit 12, an electrostatic chuck contact position obtaining unit 13, an inspection object status determining unit 14, and a controller 15 which controls each processor.

Figure 4:
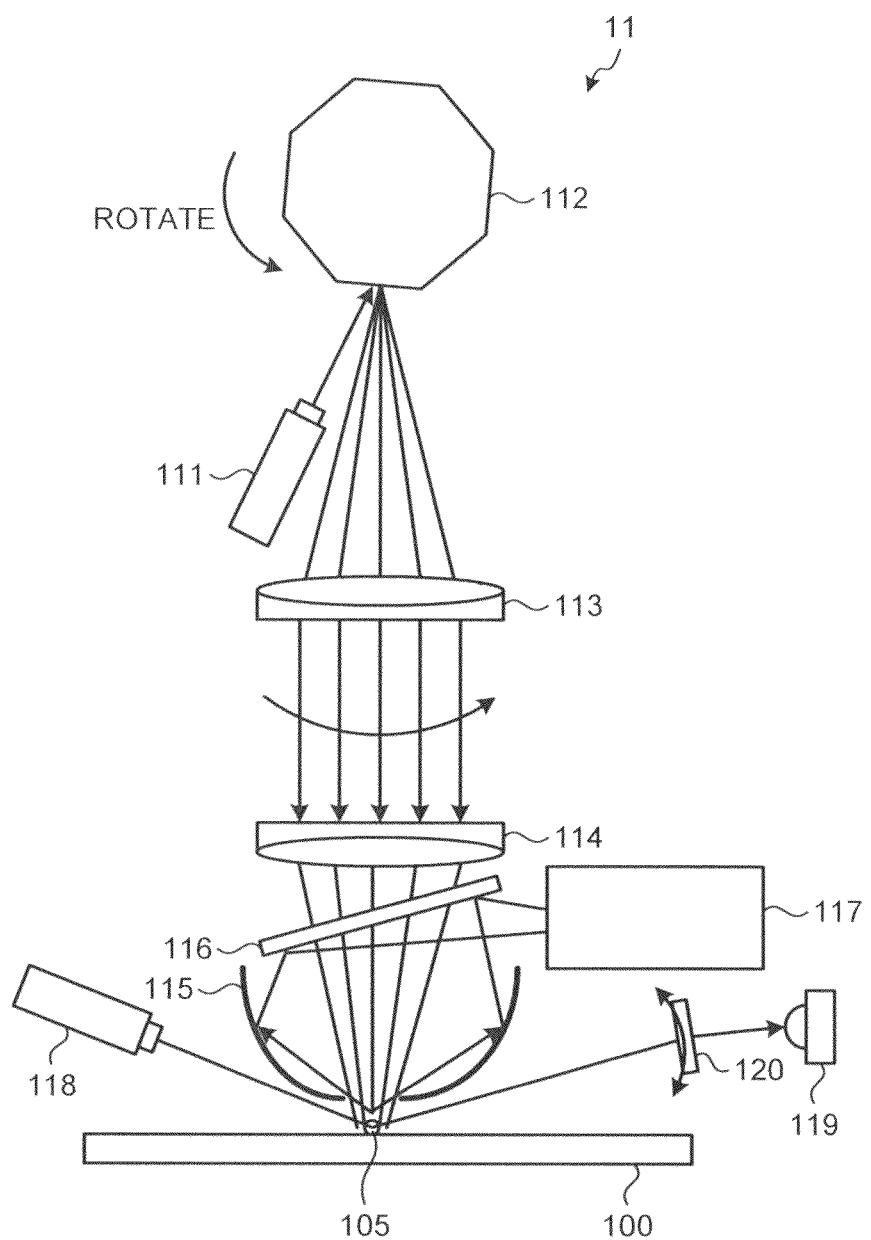
FIG. 4 is a schematic view of an example of a configuration of an inspecting unit.

The inspecting unit 11 inspects a status on a rear surface side of the electrostatic chuck holding object. A laser microscope and the like may be used, for example, as the inspecting unit 11. FIG. 4 is a schematic view of an example of a configuration of the inspecting unit. The inspecting unit 11 is provided with a laser light source 111 which emits laser light, a polygon mirror 112 which reflects the laser light from the laser light source 111, a collimator lens 113 which makes the laser light reflected by the polygon mirror 112 a parallel light beam, an objective lens 114 which focuses the laser light on a position to be inspected of the inspection object 100, a curved mirror 115 which collects the laser light scattered by the particle on the inspection object 100, a reflecting mirror 116 which guides the laser light reflected by the curved mirror 115 to a scattered light detecting unit 117, and the scattered light detecting unit 117 which detects scattered light scattered by the particle on the inspection object 100.

The inspecting unit 11 also includes a laser light source for autofocus 118 which emits laser light used for calculating a focus value, a light receiving unit for autofocus 119 which receives the laser light from the laser light source for autofocus 118 reflected by the inspection object, and a glass flat plate 120 arranged on a side of the laser light source for autofocus of the light receiving unit for autofocus 119 whose angle is adjusted such that the laser light enters the light receiving unit for autofocus 119. A controller not illustrated obtains an adjusted value of the angle of the glass flat plate 120 and calculates the focus value by using the adjusted value.

An overview of the inspection of the electrostatic chuck holding object by the inspecting unit 11 having such configuration is described. First, the mask 100 being the inspection object, for example, is put on a stage not illustrated with the rear surface up. Then, the laser light beam emitted from the laser light source 111 is reflected by the polygon mirror 112 rotating at a high speed and passes through the collimator lens 113, the objective lens 114 and the like to be applied to the inspection object. At this time, when there is a particle 105 on a position irradiated with the laser light of the inspection object, the scattered light is generated. The scattered light is collected by the curved mirror 115 and the like to be received by the scattered light detecting unit 117 through the reflecting mirror 116. Herein, an outer dimension of the particle may be measured by information such as a rotational speed of the polygon mirror 112 and a time period during which the scattered light is detected.

Inspection result information such as the particle map including information such as the position of the particle adhering to the rear surface of the inspection object, the size thereof and the like is generated by the inspection by the inspecting unit 11.

The inspection result information obtaining unit 12 obtains the inspection result information generated by the inspecting unit 11.

The electrostatic chuck contact position obtaining unit 13 obtains information of the convex portion contact region being the contact position of a surface held by the electrostatic chuck holding mechanism 50 of the inspection object (electrostatic chuck holding object) with the electrostatic chuck holding mechanism 50. Coordinate information and the like of the convex portion 53 of the electrostatic chuck holding mechanism 50 obtained from design information and the like of the electrostatic chuck holding mechanism 50, for example, may be used as the convex portion contact region information.

The inspection object status determining unit 14 determines whether there is the particle which poses an obstacle at the time of exposure process by using the inspection result information obtained by the inspection result information obtaining unit 12 and the electrostatic chuck contact position information obtained by the electrostatic chuck contact position obtaining unit 13. At this time, as described above, it is determined by using the first determining criterion value a1 in the convex portion contact region and it is determined by using the second determining criterion value a2 in the convex portion non-contact region. Meanwhile, the second determining criterion value a2 is the determining criterion value looser than the first determining criterion value a1.

According to this, it may be determined whether the particle is allowable for an EUV exposure process by using the different determining criterion values for the particle adhering to the convex portion contact region and the particle adhering to the convex portion non-contact region. Therefore, for example, even the particle having the size not allowable in the convex portion contact region becomes the allowable particle if this has a size smaller than the second determining criterion value and if this is present in the convex portion non-contact region. As a result, when the electrostatic chuck holding object is the mask, for example, the number of times of cleaning and the like may be suppressed as compared with the conventional method.

In the first embodiment, the different values are set for the convex portion contact region and the convex portion non-contact region as the allowable values of the size of the particle adhering to the electrostatic chuck holding object. According to this, there is a case in which the mask cleaning is not necessary even when the particle having the size larger than the allowable value (first determining criterion value) of the size of the particle adhering to the convex portion contact region adheres to the convex portion non-contact region. As a result, there is an effect that it becomes possible to decrease the number of times of mask cleaning in rear surface management of the electrostatic chuck holding object and to shorten a time period during which the exposure process stops while the electrostatic chuck holding object is cleaned.

Second Embodiment

In a second embodiment, a specific example of a method of obtaining a convex portion contact region and a convex portion non-contact region from information obtained as a result of rear surface inspection of an electrostatic chuck holding object is described.

Figure 5:
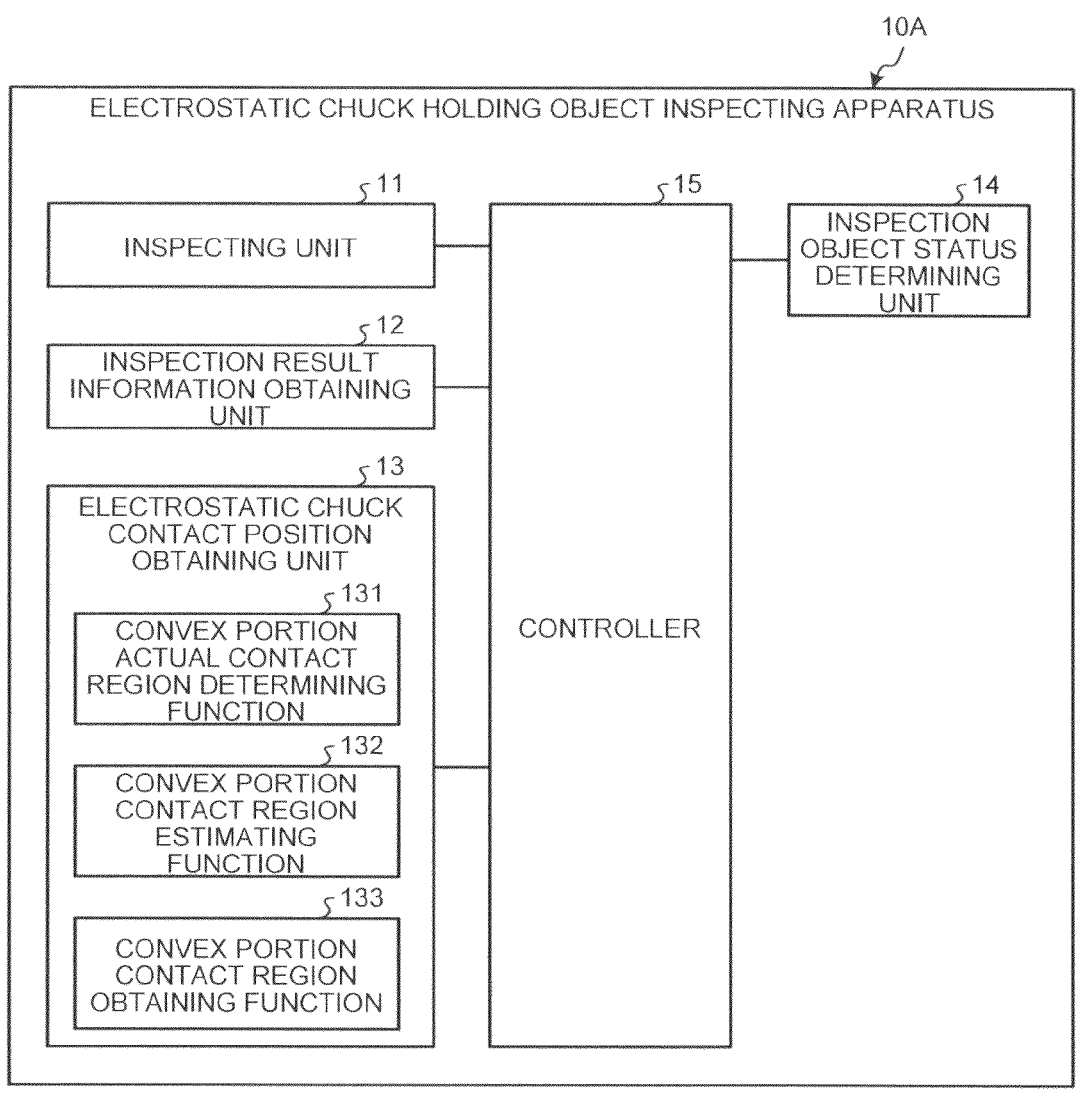
FIG. 5 is a schematic block diagram of a functional configuration of an electrostatic chuck holding object inspecting apparatus according to a second embodiment.

FIG. 5 is a schematic block diagram of a functional configuration of an electrostatic chuck holding object inspecting apparatus according to the second embodiment. An electrostatic chuck holding object inspecting apparatus 10A has a configuration in which the electrostatic chuck contact position obtaining unit 13 of the electrostatic chuck holding object inspecting apparatus 10 of the first embodiment includes a convex portion actual contact region determining function 131, a convex portion contact region estimating function 132, and a convex portion contact region obtaining function 133.

The convex portion actual contact region determining function 131 selects a plurality of positions which is estimated to be brought into contact with a convex portion 53 of an electrostatic chuck holding mechanism 50 from inspection images of a rear surface of an inspection object in inspection result information. Since the inspection image is associated with a particle map, a position on the particle map associated with the selected inspection image is the position which is estimated to be brought into contact with the convex portion 53. A trace of contact of the convex portion may be used as the position which is estimated to be brought into contact with the convex portion 53 of the electrostatic chuck holding mechanism 50.

Further, the convex portion actual contact region determining function 131 calculates an interval based on a plurality of selected positions by using a method such as a least-square method and a Fourier transform and determines that coordinates forming a regular interval on a rear surface of a mask are the convex portion actual contact regions when the calculated interval may be regarded as an integral multiple of an interval between the convex portions 53 of the electrostatic chuck holding mechanism 50.

The convex portion contact region estimating function 132 estimates a convex portion estimated contact region by using interval information of the convex portions 53 of the electrostatic chuck holding mechanism 50 described above also in a region in which there is no traces of contact with the convex portion 53 at a regular interval on the rear surface of the mask when the calculated interval may be regarded as the integral multiple of the interval between the convex portions 53 of the electrostatic chuck holding mechanism 50.

The convex portion contact region obtaining function 133 makes the convex portion actual contact region determined by the convex portion actual contact region determining function 131 and the convex portion estimated contact region estimated by the convex portion contact region estimating function 132 the convex portion contact regions.

The inspection result information obtaining unit 12 obtains the inspection result information including the inspection image taken corresponding to the position of each particle and the like on the particle map in addition to the particle map. As described above, the inspection image is associated with the position on the particle map to be stored.

Meanwhile, the same reference notes are assigned to the same component as described in the first embodiment and the description thereof is not repeated.

Figure 6:
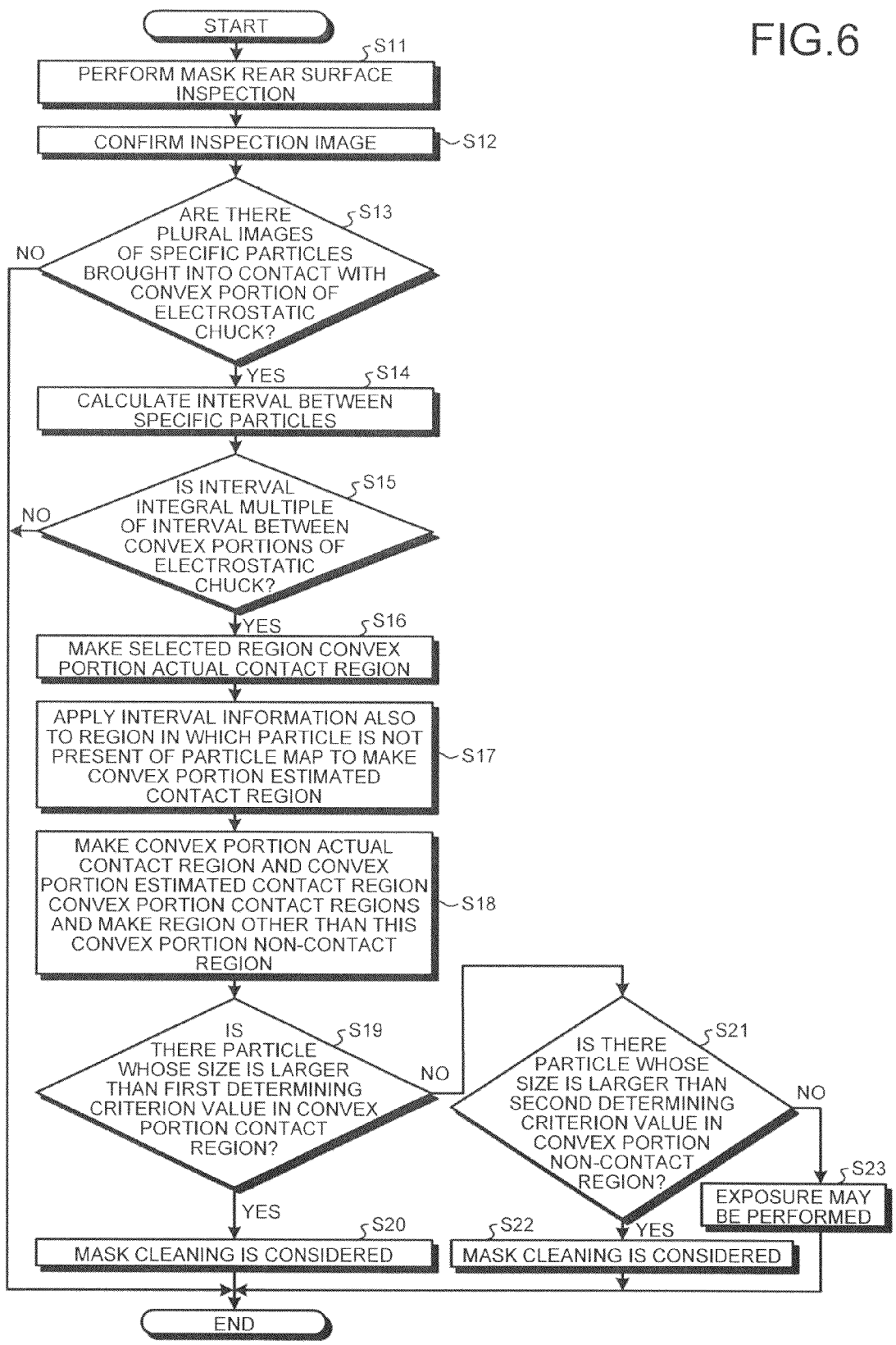
FIG. 6 is a flowchart of an example of a procedure of an electrostatic chuck holding object inspecting method according to the second embodiment.
Figure 7:
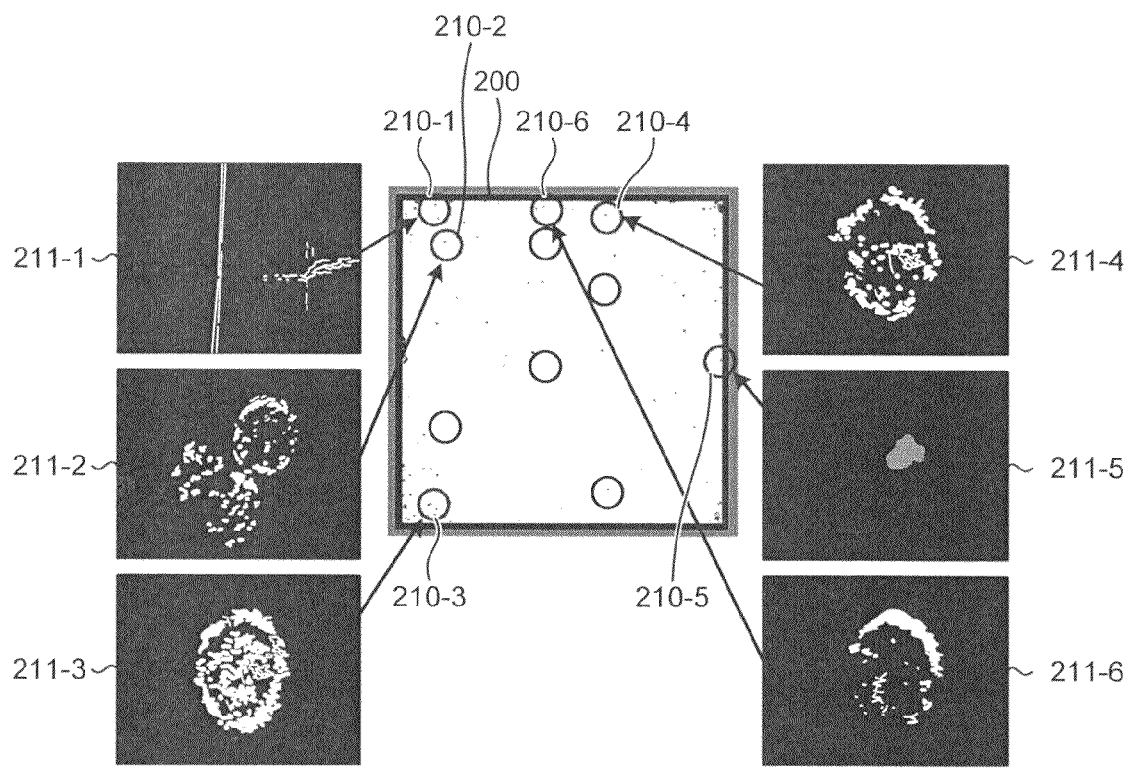
FIGS. 7 and 8 are views of an example of a method of obtaining a convex portion contact region.
Figure 8:
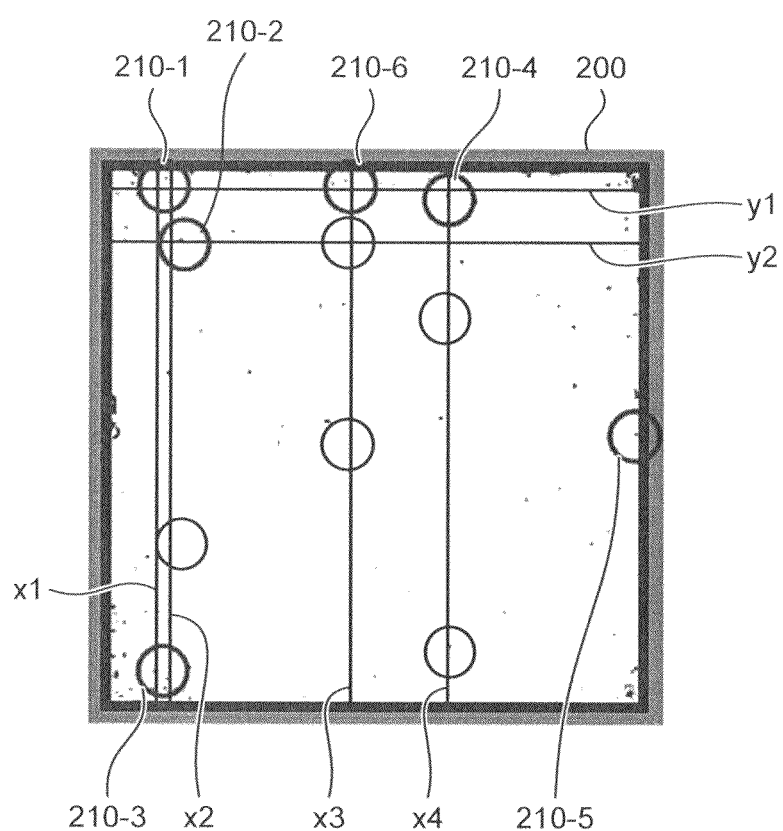

Next, a process by the electrostatic chuck holding object inspecting apparatus 10A configured in this manner is described. FIG. 6 is a flowchart illustrating an example of a procedure of an electrostatic chuck holding object inspecting method according to the second embodiment. FIGS. 7 and 8 are views illustrating an example of a method of obtaining the convex portion contact region.

First, the mask used in an EUV exposure process being the inspection object is put on a stage of the inspecting unit 11 of the electrostatic chuck holding object inspecting apparatus 10A. Next, mask rear surface inspection by the inspecting unit 11 is performed (step S11). At this time, the inspecting unit 11 makes a particle map 200 and takes inspection images 211-1 to 211-6 for the position of the particles as illustrated in FIG. 7, for example. Then, the particle map 200 and the inspection images 211-1 to 211-6 are made as the inspection result information. The inspection images 211-1 to 211-6 are obtained by taking images of positions 210-1 to 210-6 on the particle map 200, respectively.

Thereafter, an inspector confirms the inspection images (step S12) and determines whether there are a plurality of images of specific particle which is brought into contact with the convex portion 53 of the electrostatic chuck holding mechanism 50 (traces of contact) (step S13). For example, in an example in FIG. 7, the inspection image 211-1 of the position 210-1 on the particle map 200 is the image of a scratch and the like on the mask rear surface and a granular object is indicated in the inspection image 211-5 of the position 210-5. In the inspection images 211-2, 211-3, 211-4, and 211-6 of other positions 210-2, 210-3, 210-4, and 210-6, respectively, the trace of contact with the convex portion 53 of the electrostatic chuck holding mechanism 50 is indicated. The trace of contact is formed when the particle is interposed between the convex portion 53 and the mask rear surface to be crushed, for example. At a processing step, the inspection image in which such trace of contact may be confirmed is extracted from the inspection images, and it is determined that whether there is a plurality of such images.

When there is not a plurality of images of the specific particle (No at step S13), data for executing a subsequent process cannot be obtained, so that the process is finished.

On the other hand, when there is a plurality of images of the specific particle (Yes at step S13), the convex portion actual contact region determining function 131 calculates an interval between the specific particles by using the method such as the least-square method and the Fourier transform (step S14). The interval in the same direction as sides in two directions forming an outer periphery can be obtained as the interval in a case of a rectangular mask 100, for example. The convex portion actual contact region determining function 131 determines whether the calculated interval is the integral multiple of the interval between the convex portions 53 of the electrostatic chuck holding mechanism 50 (step S15). When the calculated interval is not the integral multiple of the interval between the convex portions 53 of the electrostatic chuck holding mechanism 50 (No at step S15), the calculated interval is determined not to be that by the convex portions 53 of the electrostatic chuck holding mechanism 50 and the process is finished.

When the calculated interval is the integral multiple of the interval between the convex portions 53 of the electrostatic chuck holding mechanism 50 (Yes at step S15), the convex portion actual contact region determining function 131 makes the selected region the convex portion actual contact region (step S16). The convex portion contact region estimating function 132 applies information of the calculated interval also to a region in which there is no particle of the particle map and makes the region the convex portion estimated contact region (step S17). Thereafter, the convex portion contact region obtaining function 133 makes the convex portion actual contact region and the convex portion estimated contact region the convex portion contact regions and makes a region other than this the convex portion non-contact region (step S18).

For example, FIG. 8 illustrates a state in which the interval is calculated from the positions (including the positions 210-2 to 210-4 and 210-6) of the trace of contact selected in FIG. 7 and a calculated result is drawn on the particle map 200 by a straight line. As a result, straight lines x1, x2, x3, and x4 are drawn and straight lines y1 and y2 orthogonal to the straight lines x1 to x4 are drawn on the particle map 200. Herein, an intersection between the straight line xi (i=1, 2, 3, and so on) and the straight line yj (j=1, 2, and so on) becomes the convex portion actual contact region or the convex portion estimated contact region.

Then, the inspection object status determining unit 14 determines whether there is the particle whose size is larger than a first determining criterion value in the convex portion contact region (step S19). For example, the size of the particle present in a part which becomes the convex portion actual contact region or the convex portion estimated contact region on the particle map 200 in FIG. 8 is obtained and this is compared with the first determining criterion value to be determined.

When there is the particle whose size is larger than the first determining criterion value in the convex portion contact region (Yes at step S19), mask cleaning is considered (step S20) and the process is finished.

When there is no particle whose size is larger than the first determining criterion value in the convex portion contact region (No at step S19), the inspection object status determining unit 14 further determines whether there is the particle whose size is larger than a second determining criterion value in the convex portion non-contact region (step S21). When there is the particle whose size is larger than the second determining criterion value in the convex portion non-contact region (Yes at step S21), the mask cleaning is considered (step S22) and the process is finished.

On the other hand, when there is no particle whose size is larger than the second determining criterion value in the convex portion non-contact region (No at step S21), there is no particle which poses an obstacle to the exposure process by an EUV exposure apparatus on the rear surface of the mask and exposure may be performed (step S23). Then, the electrostatic chuck holding object inspecting method is finished.

In the second embodiment, a plurality of traces of contact of the convex portions 53 is selected from the inspection images and the convex portion contact regions are obtained from the traces of contact. According to this, an effect that the convex portion contact region can be obtained for the mask with a small number of times of clamping to the electrostatic chuck holding mechanism 50 and with a small adhering amount of the particles in the EUV exposure apparatus can be obtained in addition to the effect of the first embodiment.

Third Embodiment

Although a case of obtaining a convex portion contact region by using a particle map and an inspection image is described as an example in the second embodiment, a case of obtaining the convex portion contact region by using only the particle map is described in a third embodiment.

An electrostatic chuck holding object inspecting apparatus according to the third embodiment is similar to that described in the second embodiment. However, an inspection result information obtaining unit 12 obtains only the particle map as inspection result information from an inspecting unit 11.

A convex portion actual contact region determining function 131 calculates an interval between regular particles by using a least-square method or a Fourier transform from a region in which positions of particles are regularly arranged selected by an inspector, for example, in the particle map obtained by the inspection result information obtaining unit 12 and, when the calculated interval may be regarded as an integral multiple of an interval between convex portions 53 of an electrostatic chuck holding mechanism 50, determines that coordinates forming a regular interval are the convex portion actual contact regions.

Meanwhile, other components are similar to those of the first and second embodiments, so that the description thereof is not repeated.

Figure 9:
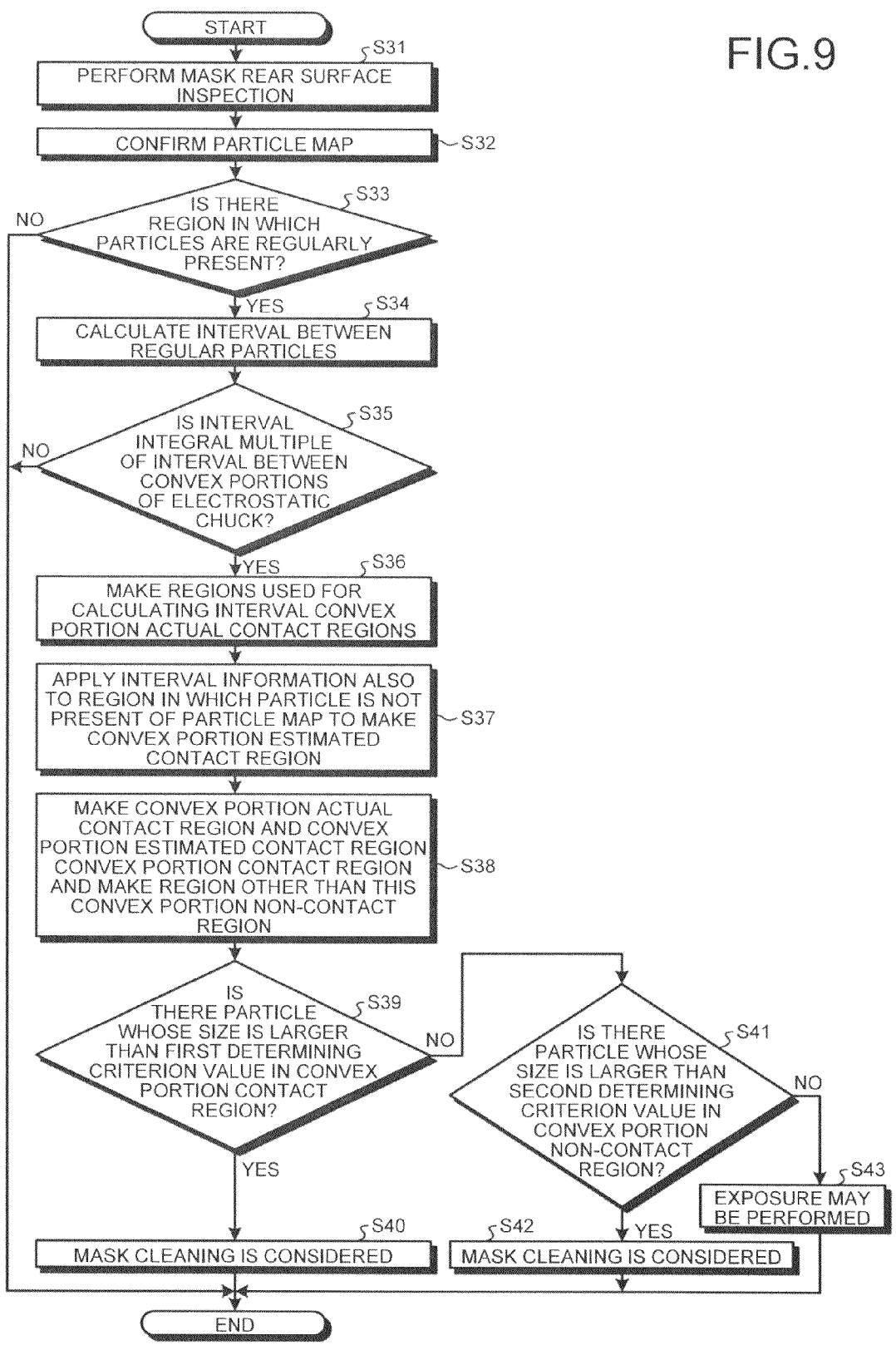
FIG. 9 is a flowchart of an example of a procedure of an electrostatic chuck holding object inspecting method according to a third embodiment.
Figure 10A:
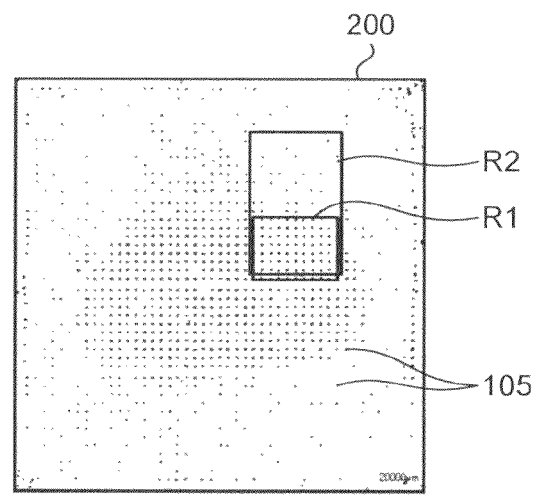
FIGS. 10A to 10C are views of an example of a method of obtaining a convex portion contact region.
Figure 10B:
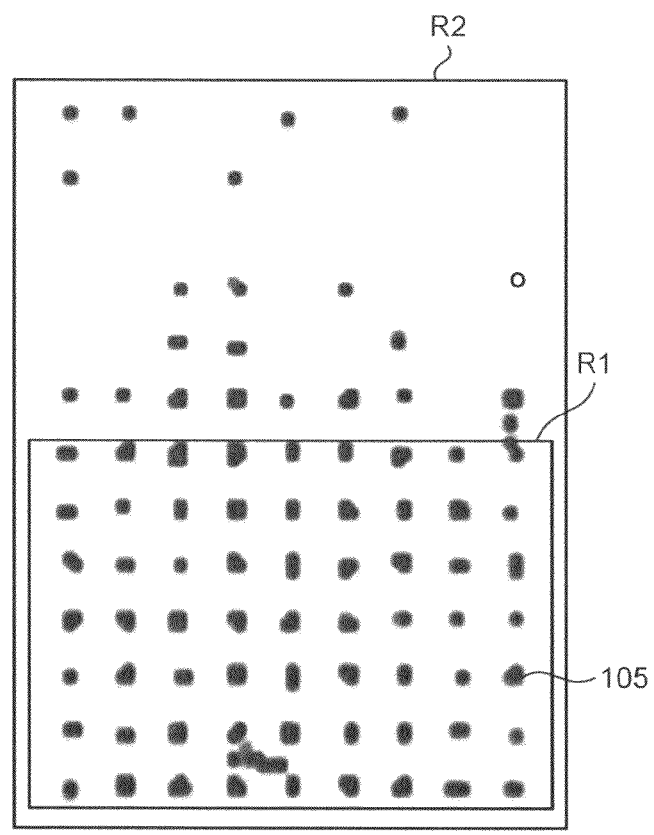
Figure 10C:
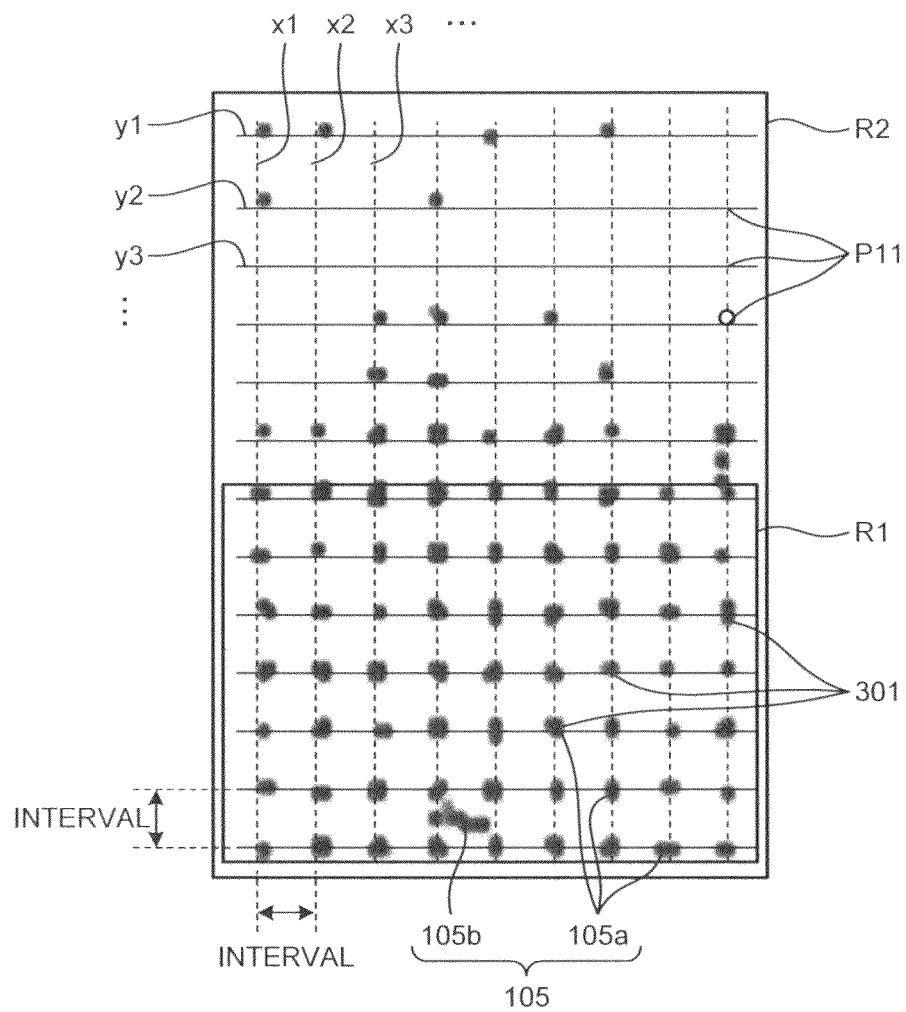

Next, a process by the electrostatic chuck holding object inspecting apparatus configured in this manner is described. FIG. 9 is a flowchart illustrating an example of a procedure of an electrostatic chuck holding object inspecting method according to the third embodiment. FIGS. 10A to 10C are views illustrating an example of a method of obtaining the convex portion contact region.

First, an inspection object is put on a stage of the inspecting unit 11. A mask used in an EUV exposure apparatus may be described as an example, for example, as the inspection object. Next, mask rear surface inspection by the inspecting unit 11 is performed (step S31). At this time, the inspecting unit 11 makes the particle map as inspection result information. FIG. 10A is an example of a particle map 200 and a particle 105 is indicated by a point in the particle map 200.

Thereafter, the inspector confirms the particle map 200 (step S32) and determines whether there is a region in which the particles 105 are regularly present (step S33). When there is no region in which the particles are regularly present (No at step S33), data for executing a subsequent process cannot be obtained, so that the process is finished.

On the other hand, when there is the region in which the particles are regularly present (Yes at step S33), the convex portion actual contact region determining function 131 calculates the interval between the regular particles by using the method such as the least-square method and the Fourier transform (step S34).

For example, in a case of FIG. 10A, the inspector selects a region R1 in which the particles 105 are regularly present from the particle map 200. Meanwhile, although the region R1 can be optionally selected, this is desirably a region in which there are many particles 105 or a region with a wide area in order to minimize an error. However, when there are many particles 105 or when the area of the region R1 is wide, it takes time to calculate the interval between the particles 105. Therefore, the region R1 is determined according to an allowable error and processing capacity of an electrostatic chuck holding object inspecting apparatus 10A.

FIG. 10B is an enlarged view of the selected region R1. The interval is calculated by using the method such as the least-square method and the Fourier transform from the particles 105 in the region R1 in FIG. 10B. The interval in the same direction as sides in two directions forming an outer periphery may be obtained as the interval in a case of a rectangular mask 100, for example.

The convex portion actual contact region determining function 131 determines whether the calculated interval is an integral multiple of the interval between the convex portions 53 of the electrostatic chuck holding mechanism 50 (step S35). When the calculated interval is not the integral multiple of the interval between the convex portions 53 of the electrostatic chuck holding mechanism 50 (No at step S35), the calculated interval is determined not to be that by the convex portions 53 of the electrostatic chuck holding mechanism 50 and the process is finished.

When the calculated interval is the integral multiple of the interval between the convex portions 53 of the electrostatic chuck holding mechanism 50 (Yes at step S35), the convex portion actual contact region determining function 131 makes the regions used for calculating the interval the convex portion actual contact regions (step S36). A convex portion contact region estimating function 132 applies information of the calculated interval also to a region in which there is no particle of the particle map and makes the region a convex portion estimated contact region (step S37). Thereafter, a convex portion contact region obtaining function 133 makes the convex portion actual contact region and the convex portion estimated contact region the convex portion contact regions and makes a region other than this a convex portion non-contact region (step S38).

For example, when the interval between the particles 105 calculated in FIG. 10B is the integral multiple of the interval between the convex portions 53 of the electrostatic chuck holding mechanism 50, a straight line connecting the particles 105 in a direction perpendicular to the direction of the calculated interval is drawn in the region R1 of the particle map 200. This is also applied to a region other than the region R1. FIG. 10C illustrates this state. In FIG. 10C, straight lines x1, x2, x3, and so on are arranged at a predetermined interval and straight lines y1, y2, y3, and so on perpendicular to the straight line xi (i=1, 2, 3, and so on) are arranged at a predetermined interval in a direction in which the straight line xi extends. Then, the region in which the particle is present at an intersection between the straight line xi and the straight line yj (j=1, 2, 3, and so on) in the region R1 becomes the convex portion actual contact region. In the region R1, a particle 105a is arranged at the intersection between the straight lines xi and yj. Therefore, the particles 105a in the region R1 used for calculating the interval are considered to be located in the convex portion actual contact regions.

The straight lines xi and yj are also applied to a region in which there is no particle 105 of a region R2 larger than the region R1 and the intersection between the straight lines xi and yj becomes a convex portion estimated contact region P11. Meanwhile, although the straight lines xi and yj are herein applied to the region R2, they are actually applied to an entire particle map 20.

The convex portion actual contact region and the convex portion estimated contact region P11 are made the convex portion contact regions. The region other than the convex portion contact region is made the convex portion non-contact region. A particle 105b is present in a region other than the intersection between the straight lines xi and yj in the region R1 in FIG. 10C.

Then, an inspection object status determining unit 14 determines whether there is the particle whose size is larger than a first determining criterion value in the convex portion contact region (step S39). When there is the particle whose size is larger than the first determining criterion value in the convex portion contact region (Yes at step S39), mask cleaning is considered (step S40) and the process is finished.

For example, in a case of FIG. 10C, it is determined whether there is the particle 105a present in the convex portion contact region whose size is larger than the first determining criterion value.

When there is no particle whose size is larger than the first determining criterion value in the convex portion contact region (No at step S39), the inspection object status determining unit 14 further determines whether there is the particle whose size is larger than a second determining criterion value in the convex portion non-contact region (step S41). When there is the particle whose size is larger than the second determining criterion value in the convex portion non-contact region (Yes at step S41), the mask cleaning is considered (step S42) and the process is finished.

For example, in a case of FIG. 10C, it is determined whether there is the particle 105b present in the convex portion non-contact region whose size is larger than the second determining criterion value. As a result of determination, when the size is not larger than the second determining criterion value, it is determined that an exposure process by the EUV exposure apparatus may be performed and when the size is larger than the second determining criterion value, the mask cleaning is considered.

On the other hand, when there is no particle whose size is larger than the second determining criterion value in the convex portion non-contact region (No at step S41), there is no particle which poses an obstacle to the exposure process by the EUV exposure apparatus on a rear surface of the mask and exposure may be performed (step S43). Then, the electrostatic chuck holding object inspecting method is finished.

In the third embodiment, the region in which the particles are regularly arranged is selected from the particle map and the convex portion contact regions are obtained from the regularly arranged particles in the region. According to this, an effect that the convex portion contact region may be obtained by using the mask with a large number of times of clamping to the electrostatic chuck holding mechanism 50 and with a large adhering amount of the particles in the EUV exposure apparatus can be obtained in addition to the effect of the first embodiment.

Fourth Embodiment

It is determined whether to use a mask according to a size of a particle adhering to a convex portion contact region and a convex portion non-contact region in the first to third embodiments. However, the particles include a hard particle made of an inorganic material and a soft particle made of an organic material, for example. The hard particle is not easily deformed, but the soft particle is easily deformed. Therefore, a size of the soft particle corresponding to an allowable value of a formed positional overlay error when a pattern is formed on a semiconductor wafer is larger than that of the hard particle. Therefore, in a fourth embodiment, a case of determining whether to clean an electrostatic chuck holding object by providing different determining criterion values for a plurality of types of particles having different properties is described.

Figure 11:
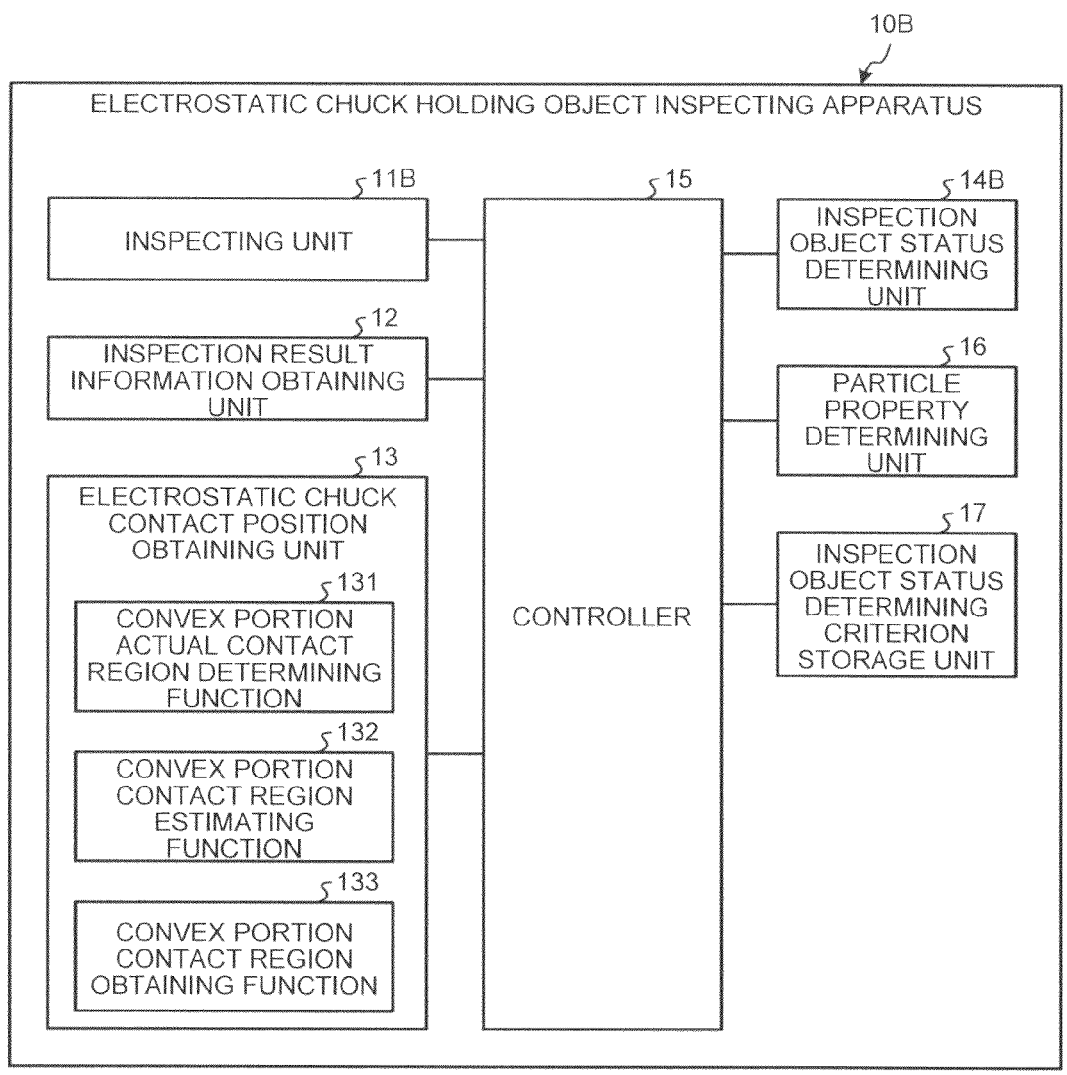
FIG. 11 is a schematic block diagram of an example of a configuration of an electrostatic chuck holding object inspecting apparatus according to a fourth embodiment.

FIG. 11 is a schematic block diagram of an example of a configuration of an electrostatic chuck holding object inspecting apparatus according to the fourth embodiment. An electrostatic chuck holding object inspecting apparatus 10B includes an inspecting unit 11B and an inspection object status determining unit 14B whose functions are different from those of the electrostatic chuck holding object inspecting apparatus 10A of the second embodiment and is further provided with a particle property determining unit 16 and an inspection object status determining criterion storage unit 17 in addition to the electrostatic chuck holding object inspecting apparatus 10A of the second embodiment.

The inspecting unit 11B has a function to analyze composition of the particle in addition to a function to make a particle map. As the function to analyze the composition of the particle, energy dispersive X-ray spectroscopy (hereinafter, referred to as EDX), a wavelength dispersive X-ray spectroscopy (WDX) or the like may be used. When there is the particle whose size is larger than a first determining criterion value in the convex portion contact region or when there is the particle whose size is larger than a second determining criterion value in the convex portion non-contact region, for example, the analysis of the composition of the particle is performed for such particle.

The particle property determining unit 16 determines whether the particle to be analyzed is a hard substance or a soft substance from a result of the composition analysis of the particle by the inspecting unit 11B. In the determination, for example, composition information of the hard substance and that of the soft substance are held and a composition result of the particle is compared with the composition information for identifying the particle. For example, as a result of the composition analysis, when the particle is a substance with a high proportion of carbon, this is determined to be the soft substance of the organic material, and when the particle is a substance without carbon contained, this is determined to be the hard substance of the inorganic material.

When there is the particle whose size is larger than the first determining criterion value in the convex portion contact region and when the particle is the soft substance from the result of the composition analysis, the inspection object status determining unit 14B performs a process to further determine whether the size of the particle in which a particle deformation amount at the time of mask clamping is taken into consideration is larger than the first determining criterion value. When there is the particle whose size is larger than the second determining criterion value in the convex portion non-contact region and when the particle is the soft substance from the result of the composition analysis, a process to further determine whether the size of the particle in which the particle deformation amount at the time of the mask clamping is taken into consideration is larger than the second determining criterion value.

As an example, the determining criterion value for the hard particle and that for the soft particle are held and it is determined by changing the determining criterion value according to the type of the particle from the result of the composition analysis.

Figure 12:
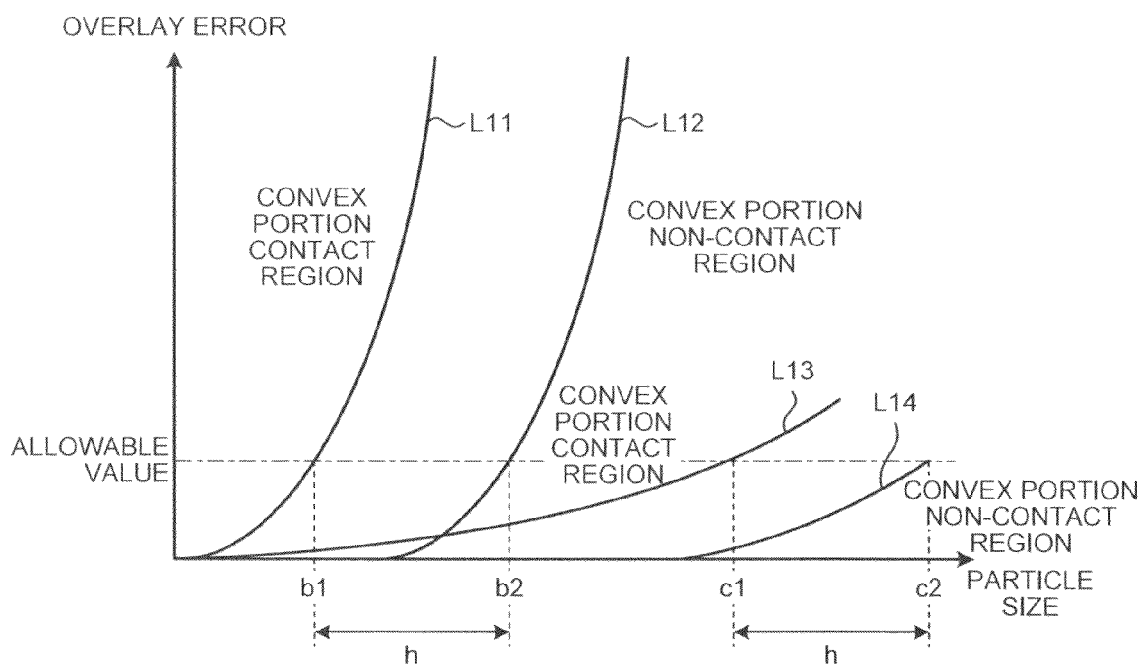
FIG. 12 is a view of an example of a concept of a determining criterion value according to the fourth embodiment.

FIG. 12 is a view illustrating an example of a concept of the determining criterion value according to the fourth embodiment. In the drawing, the size of the particle adhering to a rear surface of a mask 100 is plotted along the abscissa and an overlay error from an ideal position of a formed position of the pattern formed by an exposure process is plotted along the ordinate. A positional overlay error with respect to the particle size for the hard particle and the positional overlay error with respect to the particle size for the soft particle are indicated. As for the positional overlay error with respect to the particle size for the hard particle, there is a curved line L11 indicating the positional overlay error with respect to the particle size in the convex portion contact region and a curved line L12 indicating the positional overlay error with respect to the particle size in the convex portion non-contact region. As for the positional overlay error with respect to the particle size for the soft particle also, there are a curved line L13 indicating the positional overlay error with respect to the particle size in the convex portion contact region and a curved line L14 indicating the positional overlay error with respect to the particle size in the convex portion non-contact region. The particle size corresponding to an allowable limit value of the positional overlay error in an EUV exposure process is a first determining criterion value b1 in the convex portion contact region and a second determining criterion value b2 in the convex portion non-contact region for the hard particle, and a third determining criterion value c1 in the convex portion contact region and a fourth determining criterion value c2 in the convex portion non-contact region for the soft particle.

As illustrated in the drawing, the soft particle is deformed at the time of the mask clamping, so that the particle size corresponding to the allowable value of the positional overlay error is larger than that in a case of the hard particle.

The inspection object status determining unit 14B determines by using the first determining criterion value b1 and the second determining criterion value b2 in the case of the hard particle and determines by using the third determining criterion value c1 and the fourth determining criterion value c2 in the case of the soft particle.

Meanwhile, a determining process by the inspection object status determining unit 14B is basically similar to that described in the second embodiment, so that the detailed description thereof is not repeated.

The inspection object status determining criterion storage unit 17 stores the determining criterion value used at the time of determining process by the inspection object status determining unit 14B. In the above-described example, the first determining criterion value b1 in the convex portion contact region and the second determining criterion value b2 in the convex portion non-contact region in the case of the hard particle, and the third determining criterion value c1 in the convex portion contact region and the fourth determining criterion value c2 in the convex portion non-contact region in the case of the soft particle are stored as the inspection object determining criteria.

Meanwhile, other components are similar to those described in the first to third embodiments, so that the detailed description thereof is not repeated.

Figure 13:
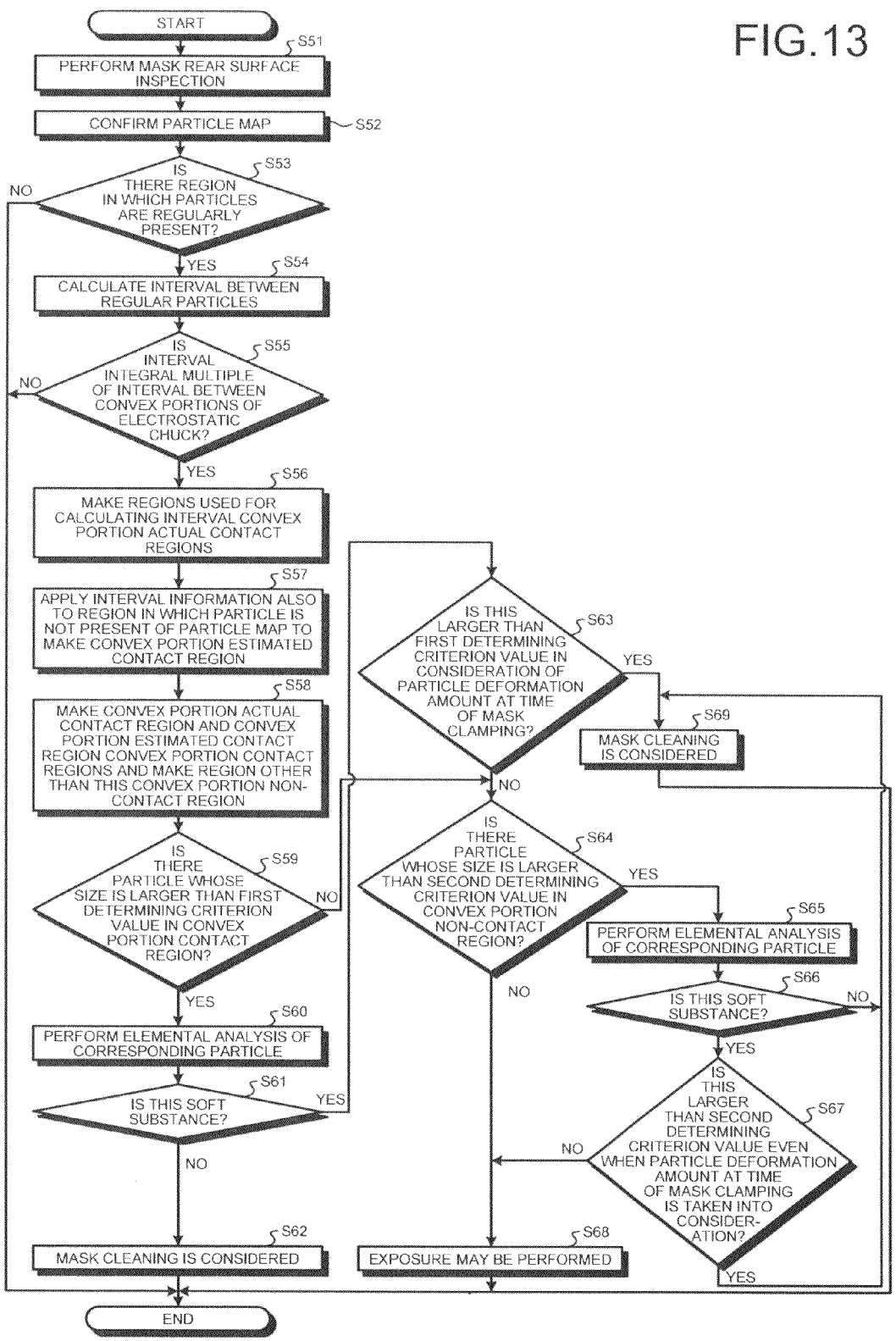
FIG. 13 is a flowchart of an example of a procedure of an electrostatic chuck holding object inspecting method according to the fourth embodiment.

Next, a process by the electrostatic chuck holding object inspecting apparatus 10B configured in this manner is described. FIG. 13 is a flowchart illustrating an example of a procedure of an electrostatic chuck holding object inspecting method according to the fourth embodiment. As at steps S31 to S38 in FIG. 9 of the third embodiment, mask rear surface inspection is performed by the inspecting unit 11B, an interval is calculated in a region in which the particles are regularly present, and the convex portion contact region and the convex portion non-contact region are obtained in an entire particle map (steps S51 to S58).

Then, the inspection object status determining unit 14B determines whether there is the particle whose size is larger than the first determining criterion value in the convex portion contact region (step S59). When there is the particle whose size is larger than the first determining criterion value in the convex portion contact region (Yes at step S59), the inspecting unit 11B performs the composition analysis (elemental analysis) of the corresponding particle (step S60). Thereafter, the particle property determining unit 16 determines whether the corresponding particle is the soft substance from the result of the composition analysis (step S61). When the particle is not the soft substance (No at step S61), that is to say, when this is the hard particle, mask cleaning is considered (step S62) and the process is finished.

When the particle is the soft substance (Yes at step S61), the inspection object status determining unit 14B determines whether the particle size is larger than the first determining criterion value even when the particle deformation amount at the time of the mask clamping is taken into consideration (step S63). Meanwhile, although the particle size in which the particle deformation amount is taken into consideration and the first determining criterion value are compared with each other, it is also possible to compare the particle size when there is the soft particle in the convex portion contact region with the third determining criterion value.

When the particle size is not larger than the first determining criterion value even when the particle deformation amount at the time of the mask clamping is taken into consideration (No at step S63), or when there is no particle whose size is larger than the first determining criterion value in the convex portion contact region at step S59 (No at step S59), the corresponding particle is regarded to have an allowable size, and thereafter, it is determined whether there is the particle whose size is larger than the second determining criterion value in the convex portion non-contact region (step S64).

When there is the particle whose size is larger than the second determining criterion value in the convex portion non-contact region (Yes at step S64), the inspecting unit 11B performs the composition analysis (elemental analysis) of the corresponding particle (step S65). Thereafter, the particle property determining unit 16 determines whether the corresponding particle is the soft substance from the result of the composition analysis (step S66). When the particle is not the soft substance (No at step S66), that is to say, when this is the hard particle, the mask cleaning is considered (step S69) and the process is finished.

When the particle is the soft substance (Yes at step S66), the inspection object status determining unit 14B determines whether the particle size is larger than the second determining criterion value even when the particle deformation amount at the time of the mask clamping is taken into consideration (step S67). Meanwhile, although the particle size in which the particle deformation amount is taken into consideration and the second determining criterion value are herein compared with each other, it is also possible to compare the particle size when there is the soft particle in the convex portion non-contact region with the fourth determining criterion value.

When the particle size is not larger than the second determining criterion value even when the particle deformation amount at the time of the mask clamping is taken into consideration (No at step S67) or when there is no particle whose size is larger than the second determining criterion value in the convex portion non-contact region at step S64 (No at step S64), there is no particle which poses an obstacle to the exposure process by the EUV exposure apparatus on the rear surface of the mask and exposure may be performed (step S68). Then, the electrostatic chuck holding object inspecting method is finished.

When the particle size is larger than the second determining criterion value when the particle deformation amount at the time of the mask clamping is taken into consideration (Yes at step S67), the mask cleaning is considered (step S69) and the process is finished.

In the fourth embodiment, the composition analysis is performed for the particle adhering to the convex portion contact region and the convex portion non-contact region whose size is larger than the determining criterion value to identify the same as the hard particle or the soft particle, and in the case of the soft particle, it is determined whether the particle size affects the EUV exposure process under a condition looser than that in the case of the hard particle. According to this, it is possible to further separate a condition to clean the mask as compared with the first to third embodiments, so that there is an effect that the number of times of mask cleaning may be decreased and a time period during which the exposure process stops while the mask is cleaned may be shortened.

Meanwhile, although the mask is described as an example of the electrostatic chuck holding object in the description above, this is not limited to the mask and may also be applied to a wafer and the like to be exposed. By inspecting the particle adhering to a rear surface of the wafer, it is possible to know a degree of contamination of the electrostatic chuck holding mechanism 50 which holds the wafer and it is possible to perform a process to clean the electrostatic chuck holding mechanism 50 when the degree of contamination is high. According to this, there is an effect that the particle may be prevented from adhering to the wafer which is put next.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An inspecting apparatus, comprising:
    a contact position obtaining unit which obtains, by using an inspection result of whether there is a particle on an inspection surface of a holding object and coordinate information of a convex portion in an electrostatic chuck holding mechanism, a contact position of the inspection surface with the convex portion; and
    an inspection status determining unit which determines whether a size of the particle adhering to a contact region in contact with the convex portion of the inspection surface is within an allowable range by using a first determining criterion value and determines whether the size of the particle adhering to a non-contact region other than the region in contact with the convex portion of the inspection surface is within an allowable range by using a second determining criterion value larger than the first determining criterion value, wherein
    the inspecting apparatus configured to inspect whether there is the particle adhering to a surface on a side in contact with the convex portion of the holding object held by the convex portion of the electrostatic chuck holding mechanism.

2. The inspecting apparatus according to claim 1, wherein the second determining criterion value is larger than the first determining criterion value by a height of the convex portion.

3. The inspecting apparatus according to claim 1, wherein the contact position obtaining unit includes:
    an actual contact region determining unit which calculates, by using coordinates of a plurality of positions estimated to be brought into contact with convex portions of the inspection surface selected from inspection images obtained by taking images of the inspection surface, an interval between the plurality of positions and makes the plurality of positions actual contact regions when the interval is an integral multiple of an interval between the convex portions;
    a contact region estimating unit which estimates an estimated contact region in contact with the convex portion in the inspection surface by using the coordinates of the actual contact regions and the calculated interval; and
    a contact region obtaining unit which obtains contact regions from the actual contact regions and the estimated contact region and makes a region other than the contact regions in the inspection surface the non-contact region.

4. The inspecting apparatus according to claim 3, wherein the actual contact region determining unit performs calculation by using a least-square method or a Fourier transform in the calculation of the interval.

5. The inspecting apparatus according to claim 1, wherein the contact position obtaining unit includes:
    an actual contact region determining unit which calculates, by using coordinates of particles in a region in which the particles are regularly arranged in a particle map indicating positions of the particles on the inspection surface, an interval between the particles and makes the positions of the regular particles actual contact regions when the interval is an integral multiple of an interval between convex portions,
    a contact region estimating unit which estimates an estimated contact region in contact with the convex portion in the inspection surface by using the coordinates of the particles and the calculated interval; and
    a contact region obtaining unit which obtains contact regions from the actual contact regions and the estimated contact region and makes a region other than the contact regions in the inspection surface the non-contact region.

6. The inspecting apparatus according to claim 5, wherein the actual contact region determining unit performs calculation by using a least-square method or a Fourier transform in the calculation of the interval.

7. The inspecting apparatus according to claim 1, wherein the inspection result includes a coordinate and a size of the particle on the inspection surface.

8. The inspecting apparatus according to claim 7, wherein the inspection result further includes an inspection image obtained by taking an image of a position of the particle on the inspection surface.

9. The inspecting apparatus according to claim 1, wherein the inspection result further includes a composition analysis result of the particle on the inspection surface, and the inspection status determining unit has a determining criterion value of the contact region and a determining criterion value of the non-contact region according to composition of the particle.

10. The inspecting apparatus according to claim 9, wherein the inspection status determining unit classifies the composition of the particle into composition of a hard particle and composition of a soft particle, determines, when an object to be determined is the hard particle and adheres to the contact region, whether a size of the particle is within an allowable range as compared with a third determining criterion value, determines, when the hard particle adheres to the non-contact region, whether the size of the particle is within an allowable range as compared with a fourth determining criterion value larger than the third determining criterion value, determines, when the object to be determined is the soft particle and adheres to the contact region, whether the size of the particle is within an allowable range as compared with a fifth determining criterion value larger than the third determining criterion value, and determines, when the soft particle adheres to the non-contact region, whether the size of the particle is within an allowable range as compared with a sixth determining criterion value larger than the fifth determining criterion value.

11. The inspecting apparatus according to claim 1, wherein the holding object is a mask of a semiconductor exposure apparatus or a wafer to be exposed.

12. The inspecting apparatus according to claim 1, wherein the holding object is a reflective mask of an EUV exposure apparatus.

13. The inspecting apparatus according to claim 1, further comprising: an inspecting unit which inspects whether there is the particle on the inspection surface of the holding object, and generates the inspection result.

14. The inspecting apparatus according to claim 13, wherein the inspecting unit further includes a function to obtain an inspection image obtained by taking an image of a position of the particle on the inspection surface.

15. The inspecting apparatus according to claim 13, wherein the inspecting unit further includes a function to analyze composition of the particle on the inspection surface.

16. An inspecting method, comprising:
    inspecting whether there is a particle on an inspection surface of a holding object;
    obtaining, by using an inspection result of the inspection and coordinate information of a convex portion in an electrostatic chuck holding mechanism, a contact position of the inspection surface with the convex portion; and
    determining whether a size of the particle adhering to a contact region in contact with the convex portion of the inspection surface is within an allowable range by using a first determining criterion value and determining whether the size of the particle adhering to a non-contact region other than the region in contact with the convex portion of the inspection surface is within an allowable range by using a second determining criterion value larger than the first determining criterion value, wherein
    the inspecting method of inspecting whether there is the particle adhering to a surface on a side in contact with the convex portion of the holding object held by the convex portion of the electrostatic chuck holding mechanism.

17. The inspecting method according to claim 16, wherein the second determining criterion value is larger than the first determining criterion value by a height of the convex portion.

18. The inspecting method according to claim 16, wherein the obtaining the contact position includes:
    calculating, by using coordinates of a plurality of positions estimated to be brought into contact with convex portions of the inspection surface selected from inspection images obtained by taking images of the inspection surface, an interval between the plurality of positions;
    making the plurality of positions actual contact regions when the interval is an integral multiple of an interval between convex portions;
    estimating an estimated contact region in contact with the convex portion in the inspection surface by using coordinates of the actual contact regions and the calculated interval; and
    obtaining contact regions from the actual contact regions and the estimated contact region and making a region other than the contact regions in the inspection surface the non-contact region.

19. The inspecting method according to claim 16, wherein the obtaining the contact position includes:
    calculating, by using coordinates of particles in a region in which the particles are regularly arranged in a particle map indicating positions of the particles on the inspection surface, an interval between the particles;
    making positions of the regular particles actual contact regions when the interval is an integral multiple of an interval between convex portions;
    estimating an estimated contact region in contact with the convex portion in the inspection surface by using coordinates of the particles and the calculated interval; and
    obtaining contact regions from the actual contact regions and the estimated contact region and making a region other than the contact regions in the inspection surface the non-contact region.

20. The inspecting method according to claim 16, wherein in the inspecting, composition of the particle on the inspection surface is further analyzed, and
    in the determining, an allowable size of the particle is determined by using a determining criterion value of the contact region and a determining criterion value of the non-contact region provided according to the composition of the particle.

* * * * *